United States Patent [19]

Arkles et al.

[11] Patent Number: 4,491,669
[45] Date of Patent: Jan. 1, 1985

[54] MIXED ALKOXYAMINOSILANES, METHODS OF MAKING SAME AND VULCANIZING SILICONS PREPARED THEREFROM

[75] Inventors: Barry C. Arkles, Oreland; William R. Peterson, Jr., Fallsington; Joseph M. Rokowski, Furlong, all of Pa.

[73] Assignee: Petrarch Systems Inc., Bristol, Pa.

[21] Appl. No.: 206,236

[22] Filed: Nov. 12, 1980

[51] Int. Cl.$^3$ ............................ C07F 7/08; C07F 7/10; C07F 7/18

[52] U.S. Cl. .................................... 556/410; 556/451; 556/457; 528/31; 528/34; 528/38

[58] Field of Search ....................... 556/410, 451, 457; 528/34, 38, 31

[56] References Cited

U.S. PATENT DOCUMENTS

| | | | |
|---|---|---|---|
| 3,030,403 | 4/1962 | Pike | 556/410 X |
| 3,047,527 | 7/1962 | Molotsky et al. | 556/410 X |
| 3,054,818 | 9/1962 | Pope et al. | 556/410 |
| 3,324,079 | 6/1967 | Spalding | 556/457 X |
| 3,467,686 | 9/1969 | Creamer | 556/410 |
| 3,927,057 | 12/1975 | Takamizawa et al. | 556/410 X |

OTHER PUBLICATIONS

"Chemical Abstracts Registry Handbook", No. Section, 1965–1971, Nos. 17800-00-9 to 22799-89-9, American Chemical Society, Columbus, 1975, pp. 6234R and 6242R.
Noll, "Chemistry and Technology of Silicones", Academic Press, N.Y., p. 81, 1968.
K. Moedritzer and J. R. Van Wazer, "Redistribution Equilibria on Dimethylsilicon", *Inorganic Chemistry* 7:2105–2107, (1968).
K. Moedritzer and J. R. Van Wazer, "Scrambling of Methoxyl, Dimethylamino, and Chloro Groups on Silicon", *Inorganic Chemistry* 3:268–272, (1968).
J. R. Van Wazer and K. Moedritzer, "Scrambling of Methoxyl, Dimethylamino and Chloro Groups on the Methyl- and Dimethylsilicon Moieties", *Journal of Inorganic Nuclear Chemistry* 26:737–744, (1964).
S. S. Washburne and William R. Peterson, "Chloraminosilanes: I. The Preparation of Chloro (dimethylamino) hydrogen Silanes", *Inorganic Nuclear Chemistry Letters* 5:17–19, (1969).

Primary Examiner—Paul F. Shaver
Attorney, Agent, or Firm—Panitch, Schwarze, Jacobs & Nadel

[57] ABSTRACT

The preparation of pure mixed alkoxyaminosilanes is described corresponding to the general formula:

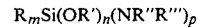

$$R_m Si(OR')_n (NR''R''')_p$$

wherein:
R is hydrogen, short chain alkyl or alkenyl or aryl;
R" and R''' are separately either hydrogen, short chain alkyl or aryl, at least one being other than hydrogen;
R' is short chain alkyl or aryl; and
m, n and p are integers such that m+n+p=4 and n and p are at least one each.

The obtained compounds are employed in endcapping of polysiloxanes having terminal silane groups.

25 Claims, No Drawings

MIXED ALKOXYAMINOSILANES, METHODS OF MAKING SAME AND VULCANIZING SILICONS PREPARED THEREFROM

BACKGROUND OF THE INVENTION

The present invention is directed to the preparation in pure state of organosilane compounds containing at least one amino substituent and at least one oxyaliphatic or oxyaromatic group attached directly to silicon. The invention includes the compounds thus formed, the methods of making them and the polymeric products obtained by their reaction with certain silicone polymers.

The relatively uncomplex molecules which can be described as mixed organoalkoxyaminosilanes and alkoxyaminosilane hydrides have not heretofore been isolated as pure materials, nor have such compounds been characterized. Prior publications offer evidence that compounds of this class could not be isolated as pure products since they were subject to random scrambling reactions (See Moedritzer, K. and Van Wazer, J. R., *Journal of Inorganic Nuclear Chemistry* 26:737 (1964); *Inorganic Chemistry* 3:268 (1964); *Inorganic Chemistry* 7:2105 (1968). These authors reported in the cited 1968 reference, for example, that the following is an equilibrium reaction:

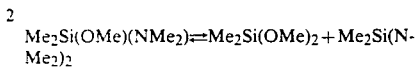
$$Me_2Si(OMe)(NMe_2) \rightleftharpoons Me_2Si(OMe)_2 + Me_2Si(NMe_2)_2$$

wherein Me is a methyl group (—CH$_3$). They were unable to obtain spectra of the pure compounds since they could not isolate these, but they did make assignments based on the obtained mixtures.

The first of the above-cited publications discloses calorimetric and kinetic results indicating that the presence of a methyl group increased the rate of exchange 20 to 200 fold. When two or more methyl groups were present, the exchange rate was so great that these authors could not measure it. The distribution of alkoxy and amino groups on the silanes was shown to be random. In the case of the mixed chloroaminosilanes, on the other hand, although exchange was reported, the distribution appeared to be non-random. From the foregoing evidence, it would appear, although unlikely, that the mixed chloroaminosilanes might be isolated, while the mixed alkoxy aminosilanes certainly could not be isolated. One of the present inventors indeed was able to isolate and distill mixed chloroaminosilanes (Washburne, S. S. & Peterson, W. R., *Inorganic Nuclear Chemistry Letters* 5:17 (1969). Initial attempts to prepare the mixed alkoxyaminosilanes, however, were not fruitful, thus substantiating the evidence presented by Moedritzer and Van Wazer in support of their argument that such preparation of the pure mixed alkoxyaminosilanes was not possible.

BRIEF SUMMARY OF THE INVENTION

Despite previously expressed beliefs to the contrary, it has now been found in accordance with the present invention that mixed alkoxyaminosilanes can be prepared and isolated in pure form, free of redistribution products. This has been accomplished by two general types of preparative methods. Thus, in one such method the desired number of chlorine groups is removed from a parent chlorine compound by alcoholysis and the remaining chlorine is replaced by reaction with an amine compound. In the second of these methods, one or more amino groups of a an amine substituted silane compound are replaced by reaction with an alcohol. To assure the purity of the desired reaction product, precautions should be taken to prevent certain types of contaminations during the course of the preparative reactions and in the final product. Thus, metallic salt impurities, such as halides of aluminum, iron, copper and zinc should be avoided, as well as alkali metal hydroxides and water.

The pure mixed alkoxyaminosilanes obtained by the methods of the present invention are useful in the preparation of silicone polymers, while the prior random mixtures cannot be successfully employed for this purpose.

DETAILED DESCRIPTION OF PREFERRED EMBODIMENTS

The mixed alkoxyaminosilanes prepared in accordance with the present invention correspond to the general formula:

$$R_mSi(OR')_n(NR''R''')_p \qquad (I)$$

wherein:
R is hydrogen, short chain alkyl or alkenyl of up to eight carbon atoms, or aryl, such as phenyl, R being preferably methyl, ethyl or vinyl;
R'' and R''' are separately either hydrogen, short chain alkyl or aryl, at least one being other than hydrogen;
R' is a short chain alkyl or aryl; and
m, n and p are integers such that m+n+p=4 and n and p are at least one each.

From the above, it is evident that the present invention includes mixed aryloxyaminosilanes, but for ease of reference the term "mixed alkoxyaminosilanes" will be understood to include both alkoxy and aryloxy compounds unless the context indicates otherwise.

These compounds are prepared in pure form by either of two methods: (1) alcoholysis of a chlorosilane compound to replace one or more of the chlorine groups with alkoxy or aryloxy and then replacing the remaining chlorine by reaction with a twice molar excess of an amino compound; or (2) by replacing one or more amino groups of a multiply amine substituted silane compound by reaction with an alcohol. These reactions are exemplified by the following simplified general equations:

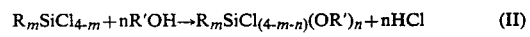
$$R_mSiCl_{4-m} + nR'OH \rightarrow R_mSiCl_{(4-m-n)}(OR')_n + nHCl \qquad (II)$$

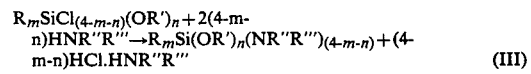
$$R_mSiCl_{(4-m-n)}(OR')_n + 2(4-m-n)HNR''R''' \rightarrow R_mSi(OR')_n(NR''R''')_{(4-m-n)} + (4-m-n)HCl \cdot HNR''R''' \qquad (III)$$

and

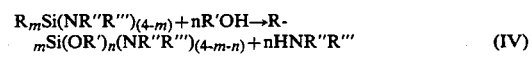
$$R_mSi(NR''R''')_{(4-m)} + nR'OH \rightarrow R_mSi(OR')_n(NR''R''')_{(4-m-n)} + nHNR''R''' \qquad (IV)$$

wherein R, R', R'', R''', m and n are as defined above. It will be understood that R in the final products in equations II and III above may be replaced by OR' or NR''R''' groups. It should also be noted that (4-m-n)=p, and that it is necessary to add twice the amount of amine desired to be added to the alkoxychorosilane in Equation III, since the amine also forms an amine hydrochloride. Although the chloro compounds are preferred in the above reactions due to economics, other halogenated or similar starting materials could be substituted.

The following specific examples illustrate preferred procedures for practice of the invention, without however being limited thereto.

In all of the examples which follow, the glassware employed was of the borosilicate type which was initially soaked in 1% hydrofluoric acid for a minimum of two hours. It was then rinsed twice with acetone, once with hexane and dried with a nitrogen purge. This procedure removes high surface concentrations of boron, aluminum and alkali metals. All chlorosilanes were redistilled in glass in order to reduce iron and copper impurities below 10 ppm. In general, concentrations of iron, copper and aluminum in the reaction mixture should not exceed 100 ppm. The reactions were all run under dry conditions in a nitrogen atmosphere.

EXAMPLE 1

Methyl(dimethylamino)ethoxysilane

A 3 neck 5 L. flask equipped with a mechanical stirrer, an addition funnel to which a nitrogen bubbler is attached and a high efficiency tube-in-shell water-cooled condensor was charged with 2 liters of pentane and 416 mls of methyldichlorosilane. The mixture was heated to reflux and 224 mls of anhydrous ethanol was added over two hours. The mixture was refluxed for one hour to remove the last of the hydrogen chloride byproduct. The mixture was then cooled to 10°-15° C. in a tap water bath. The water-cooled condensor was replaced with a dry ice-acetone condensor. 550 mls of dimethylamine was condensed and then added through the addition funnel. The addition required two hours. Large volumes of white salts appeared immediately. The mixture was stirred for an additional two hours. It was then filtered by means of a fiberglass filter stick. The salts were washed twice with 1 liter of pentane. Distillation through a 75 cm packed column yielded 385 g of methyl(dimethylamino)ethoxysilane (b.p. 100°-101° C.). The product was identified by IR. On contact with water it reacted within seconds to yield a white cross-linked solid.

EXAMPLE 2

Diethoxy(dimethylamino)silane

Following the same general procedure described in Example 1, 2 liters of pentane and 404 mls of trichlorosilane were charged in a 5 L flask. During reflux, 464 mls of anhydrous ethanol was added dropwise. After the alcoholysis was completed, 550 mls of dimethylamine was added to the unisolated diethoxychlorosilane. Distillation yielded 290 g of diethoxy(dimethylamino)silane (b.p. 138°-139° C.).

EXAMPLE 3

Methyldiethoxy(dimethylamino)silane

As described in Example 2, 4 moles (467 mls) of methyltrichlorosilane was charged along with 2 liters of pentane into a 5 L flask. At reflux, 8 moles (464 mls) of anhydrous ethanol was slowly added while the HCl was vented through the condensor. Reaction with approximately 8.5 moles (550 ml) of dimethylamine yielded 514 g of methyldiethoxy(dimethylamino)silane (b.p. 147° C.) upon distillation.

EXAMPLE 4

Methyl[bis(dimethylamino)]ethoxysilane

Under the general conditions described above, 2 moles of methyltrichlorosilane were subjected to alcoholysis by an equimolar amount of anhydrous ethanol. Reaction with approximately 8.5 moles of dimethylamine, subsequent filtration and distillation yielded 212 g of methyl[bis(dimethylamino)]ethoxysilane (b.p. 154° C.).

EXAMPLE 5

Dimethoxy(dimethylamino)silane

The reaction conditions were identical to those described in Example 2 except anhydrous methanol was substituted for anhydrous ethanol. The reaction yielded 156 g of dimethoxy(dimethylamino)silane (b.p. 118°-120° C.).

EXAMPLE 6

Methyldimethoxy(dimethylamino)silane

The reaction conditions were identical to those described in Example 3 except anhydrous methanol was subtituted for anhydrous ethanol. The reaction yielded 399 g of methyldimethoxy(dimethylamino)silane (b.p. 121°-124° C.).

EXAMPLE 7

Vinyldiethoxy(dimethylamino)silane

As described in Example 2, 4 moles (520 mls) of vinyltrichlorosilane was charged along with 2 liters of pentane into a 5 L flask. At reflux, 8 moles (464 mls) of anhydrous ethanol was slowly added while HCl was vented through the condensor. Reaction with approximately 8.5 moles (550 ml) of dimethylamine yielded 224 g of vinyldiethoxy(dimethylamino)silane upon distillation (b.p. 163°-164° C.).

The analogous phenyl compounds are obtained by the procedures described above when starting with phenyl silane halides instead of an alkyl silane halide. Among other examples of starting materials included, but not limited thereto, are: dichlorosilane, dimethyl- or diethyldichlorosilane, dihexyldichlorosilane; allylmethyl dichlorosilane, allyltrichlorosilane, n-amylmethyldichlorosilane, t- and n-butylmethyldichlorosilane, t-butylphenyldichlorosilane, t-butyltrichlorosilane, diallyldichlorosilane, dibutyldichlorosilane, methylcyclohexyldichlorosilane, phenyltrichlorosilane, diphenyldichlorosilane.

To obtain the analogous compounds wherein R' of the general formula (I) above is phenyl, the initial reaction of equation (II) is carried out by employing a phenol instead of an alcohol.

For the reaction of equation (III), it is preferred to employ a short chain dialkylamine, particularly dimethyl or diethylamine.

The second method for practice of the invention, starting with an amine substituted silane compound, is illustrated by the following example.

EXAMPLE 8

Dimethyl(dimethylamino)ethoxysilane

A 2 L 3 neck flask equipped with a magnetic stirrer, Frederich's condensor and an addition funnel was charged with 361 mls of bis(dimethylamino)dimethylsilane and an equal volume of tetrahydrofuran. At ambient temperature, 116 mls of anhydrous ethanol was added over one hour. Dimethylamine evolved. The mixture was transferred to a single neck flask and distilled. 264 g of dimethyl(dimethylamino)ethoxysilane, (b.p. 115°-118° C.), was recovered.

Instead of the starting amino silane compound specified in Example 8, one may employ bis(dimethylamino)methylvinylsilane, tetrakis(diethylamino)silane, methyl [tris(cyclohexylamino)]silane, and others which will be apparent to one skilled in the art in view of this disclosure.

The pure mixed alkoxyaminosilanes of the present invention find use in the preparation of silicone polymers, particularly those used in RTV compositions, while the earlier known random mixtures do not. Among such useful polymers are those formed by reaction of a silanol terminated polysiloxane with an aminosilane, resulting in endcapping of the polysiloxane and obtaining products which are vulcanizable by condensation or vinyl addition cures. The general endcapping reaction is illustrated by the reaction shown in the following equation, employing methyl (dimethylamino)ethoxysilane, for example:

$$H\text{-}(OSiMe_2)_n\text{-}OH + 2MeHSi(OEt)(NMe_2) \rightarrow MeHSi(OEt)\text{-}(OSiMe_2)_n\text{-}OSiMeH(OEt) + 2HNMe_2 \quad (V)$$

wherein Me is methyl, Et is ethyl and n indicates the number of units in the polymer chain.

The terminal groups of the endcapped products may be utilized in either of the following crosslinking reactions, for example:

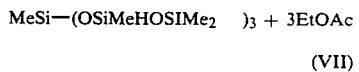

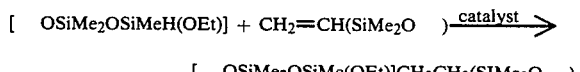

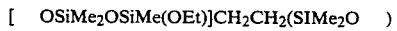

The examples below illustrate, without being limited to these particular reagents, reactions of the mixed alkoxyaminosilanes with silanol terminated silicone polymers to yield products useful for room temperature vulcanizing (RTV) compositions.

EXAMPLE 9

A solution of 200 g of silanol terminated polydimethylsiloxane (viscosity of 2000 ctsk and $Mn \approx 22{,}000$) and 500 ml toluene was charged in a 3 L flask. 3.26 g of diethoxy(dimethylamino)silane was added and the flask warmed to 40° C. for two hours. The toluene was removed by rotary evaporation. The stripping was continued until the polymer was subjected to 80° C. at 15 mm. The product was identified by IR as the $\alpha\omega$(diethoxyhydrosilyl)polydimethylsiloxane.

EXAMPLE 10

Under conditions described in Example 9, a silanol terminated fluid with a viscosity of 12,500 ctsk and an $Mn \approx 40{,}000$ was reacted with a 2.5 mole stoichiometry of vinyldiethoxy(dimethylamino)silane. The product was identified by IR as $\alpha\omega$(vinyldiethoxysilyl)polydimethylsiloxane.

The polysiloxane compounds obtained using the mixed alkoxyaminosilane intermediates of the invention for endcapping can be employed in the same manner and for the same purposes as the known prior polysiloxanes of the lower molecular weight fluid type as well as the higher molecular weight elastomeric resin species. They have good resistance to water and oxidation, are stable over a wide temperature range, and have good lubricity. They find use as hydraulic fluids, antifoaming agents, lubricating greases and water-repellant coatings. An important use for these polysiloxanes is as encapsulating materials for electronic devices.

The present invention may be embodied in other specific forms without departing from the spirit or essential attributes thereof and, accordingly, reference should be made to the appended claims, rather than the foregoing specification, as indicating the scope of the invention.

We claim:

1. Compounds of the formula $$R_mSi(OR')_n(NR''R''')_p$$

wherein:

R is hydrogen, short chain alkyl or alkenyl or aryl group;

R'' and R''' are each short chain alkyl;

R' is short chain alkyl or aryl, at least one R' being ethyl; and m, n and p are integers such that $m+n+p=4$, and m, n, and p are at least one each.

2. Compounds according to claim 1 wherein at least one R substituent is methyl or ethyl.

3. Compounds according to claim 1 wherein p is one and R'' and R''' are each methyl.

4. Compounds according to claim 1 wherein m is 2 and each R component is methyl.

5. Methyl(dimethylamino)ethoxysilane.

6. Diethoxy(dimethylamino)silane.

7. Methyldiethoxy(dimethylamino)silane.

8. Methyl[bis(dimethylamino)]ethoxysilane.

9. Dimethoxy(dimethylamino)silane.

10. Dimethyl(dimethylamino)ethoxysilane.

11. Vinyldiethoxy(dimethylamino)silane.

12. The method of preparing pure organosilane compounds having directly attached to the silicon atom thereof at least one amino group and at least one alkoxy or aryloxy group, which comprises:

(a) redistilling in glass a polychlorosilane compound to reduce iron and copper impurities to below ten parts per million, (b) decontaminating reaction glassware to remove high surface concentrations of boron, aluminum and alkali metals such that concentrations of iron, copper and aluminum in the reaction mixture do not exceed one hundred parts per million, (c) reacting in said decontaminated reaction glassware said redistilled polychlorosilane compound with an anhydrous alcohol under conditions to replace at least one chloro with an alkoxy or aryloxy group, and (d) reacting the product obtained in step (c) with an amino compound.

13. The method of preparing pure organosilane compounds having directly attached to the silicon atom thereof at least one amino group and an alkoxy or aryloxy group, which comprises:

(a) decontaminating reaction glassware to remove high surface concentrations of boron, aluminum and alkali metals such that concentrations of iron, copper and aluminum in the reaction mixture do not exceed one hundred parts per million, and (b) reacting in said decontaminated reaction glassware an organosilane compound, having at least two amino substituents directly attached to the silicon atom, with an anhydrous alcohol to replace one of said amino substituents by an alkoxy or aryloxy group.

14. The method according to claim 12 wherein said amino compound is a dialkylamine having short chain alkyl groups.

15. The method according to claim 12 wherein said amino compound is dimethylamine.

16. The method according to claim 12 wherein said polychlorosilane is an alkyldichlorosilane.

17. The method according to claim 12 wherein said polychlorosilane is trichlorosilane.

18. The method according to claim 12 or 17 wherein said polychlorosilane is an alkyltrichlorosilane.

19. The method according to claim 12 wherein said polychlorosilane is a trichloro compound and is reacted with two moles alcohol per mole of said trichlorosilane.

20. The method according to claim 12 wherein said amino compound is added to the reaction in an amount of twice the amount of amine group desired to be added to the product of step (c).

21. The method of claim 13 wherein said alcohol is ethanol.

22. The method of claim 13 or 21 wherein said amino-containing organosilane compound is bis(dimethylamino)dimethylsilane.

23. The product identified as $\alpha\omega$(diethoxyhydrosilyl)polydimethylsiloxane.

24. Compounds of the formula $$R_m Si(OR')_n (NR''R''')_p$$

wherein:
R is hydrogen, short chain alkyl or alklenyl or aryl group, at least one R being vinyl;
R'' and R''' are each short chain alkyl;
R' is short chain alkyl or aryl; and
m, n and p are integers such that $m+n+p=4$, and m, n and p are at least one each.

25. A method comprising endcapping a silane terminated polysiloxane by reaction with a silane compound of the formula $$R_m Si(OR')_n (NR''R''')_p$$

wherein:
R is hydrogen, short chain alkyl or alkenyl or aryl group;
R'' and R''' are each short chain alkyl;
R' is short chain alkyl or aryl; and
m, n and p are integers such that $m+n+p=4$, and m, n and p are at least one each.

* * * * *